United States Patent [19]

Battaglia et al.

[11] Patent Number: 4,669,461
[45] Date of Patent: Jun. 2, 1987

[54] DEVICE FOR ADMINISTERING OXYGEN TO INFANTS DURING NURSING

[75] Inventors: Maryann Battaglia, 2865 Randall Ave., White City, Oreg. 97503; John P. Diskin, Talent, Oreg.

[73] Assignee: Maryann Battaglia, White City, Oreg.

[21] Appl. No.: 895,340

[22] Filed: Aug. 11, 1986

[51] Int. Cl.$^4$ ............................................. A61M 15/00
[52] U.S. Cl. ........................... 128/202.15; 128/200.24; 128/207.18; 128/150; 128/912; 128/202.13
[58] Field of Search ..................... 128/200.14, 200.24, 128/202.13, 203.12, 203.29, 204.18, 205.25, 206.12, 206.28, 207.13, 207.14, 207.15, 207.16, 207.17, 207.18, 912, 914

[56] References Cited

U.S. PATENT DOCUMENTS

| | | | |
|---|---|---|---|
| 2,012,441 | 8/1935 | Willson et al. | 128/205.25 |
| 3,316,907 | 5/1967 | Gorpil | 128/205.25 |
| 4,454,877 | 6/1984 | Miller et al. | 128/202.13 |
| 4,520,809 | 6/1985 | de Greef et al. | 128/207.18 |

FOREIGN PATENT DOCUMENTS 2848645 5/1979 Fed. Rep. of Germany ........................ 128/207.14

Primary Examiner—Henry J. Recla
Attorney, Agent, or Firm—John F. Ingman

[57] ABSTRACT

A device for administering oxygen to infants during nursing which provides an oxygen flow-directing member, in half-funnel shape, which includes an inlet opening for connection to oxygen-supplying tubing, an internal plate with a plurality of holes for oxygen flow regulation, and a semicircular outlet. The flow-directing member is attached to the nursing source in two configurations, a bottle feeding configuration and a breast feeding configuration. In the bottle feeding configuration, the flow-directing member is attached to the neck of the feeding bottle by a partial neck-encircling foam collar with adhesive tabs. In this configuration, the flow-directing member may rotate about a pair of rivet-like fasteners connected to the foam collar, so as to pivot forwards and backwards on the bottle, for adjustably directing the oxygen flow directing upon the nursing infant's nostrils. In the breast configuration, an adhesive, breast-conforming pad is utilized to mount the flow-directing member, a single rivet-like fastener being used to achieve turret-like movement for adjustable direction of the flow of oxygen.

10 Claims, 9 Drawing Figures

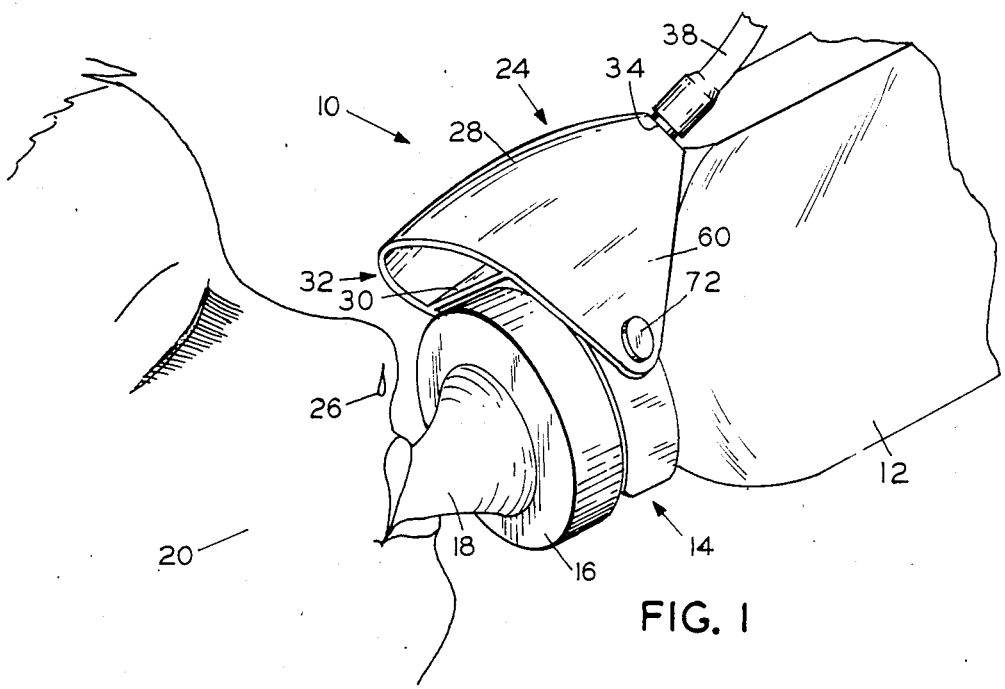
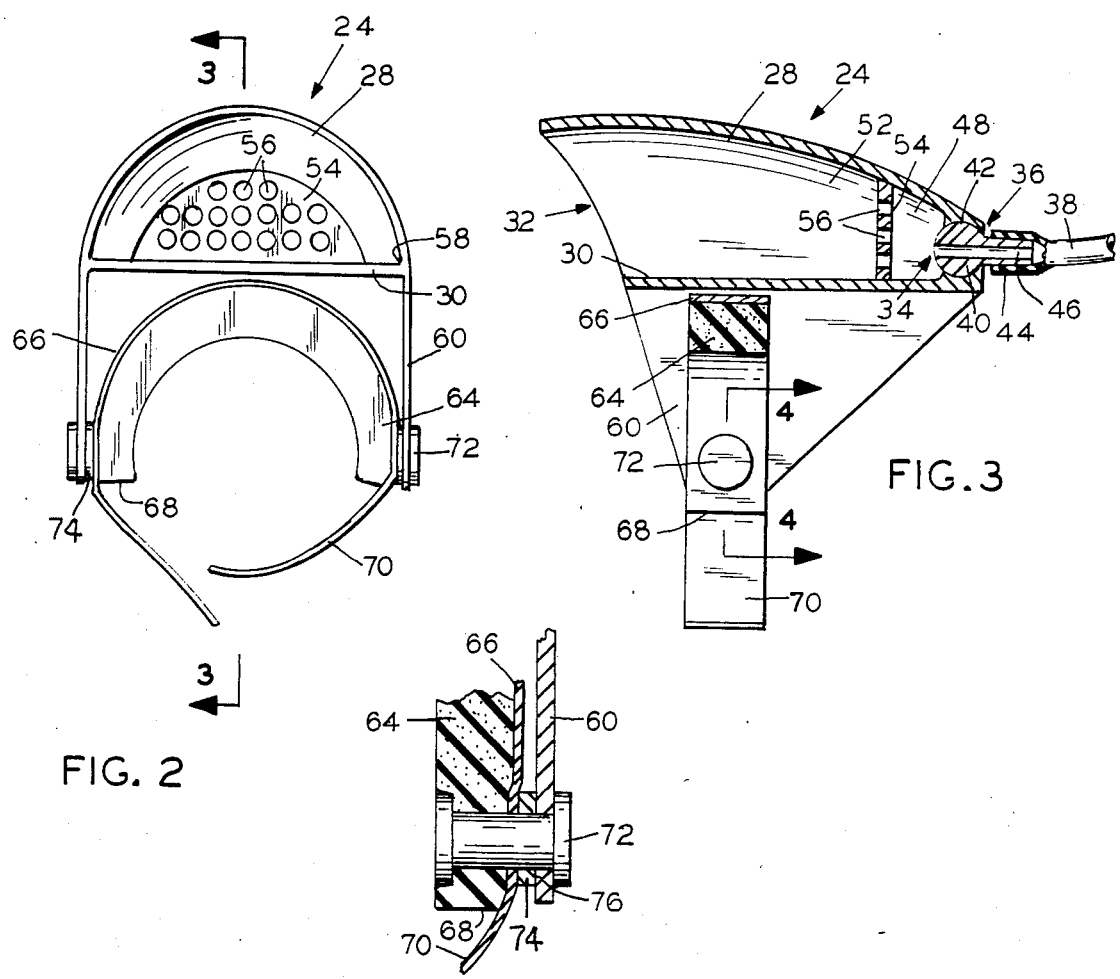

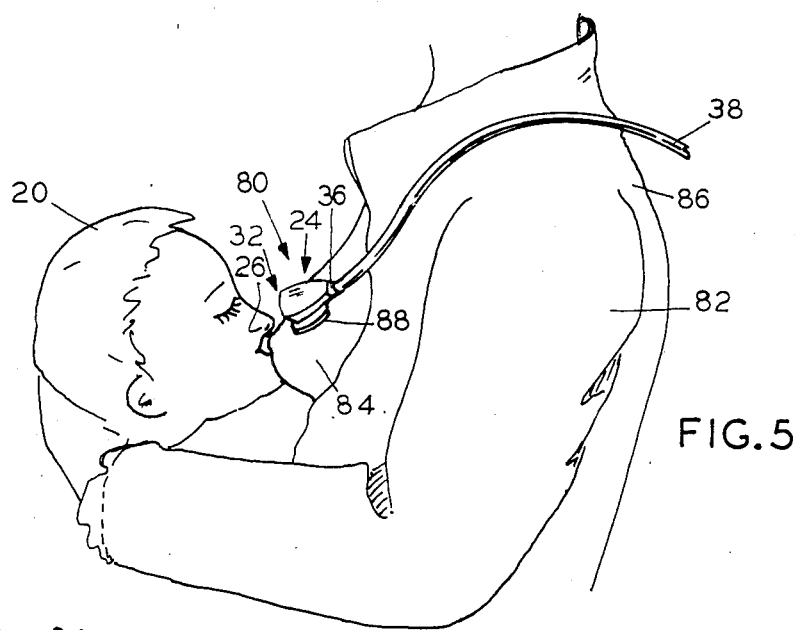
FIG. 5
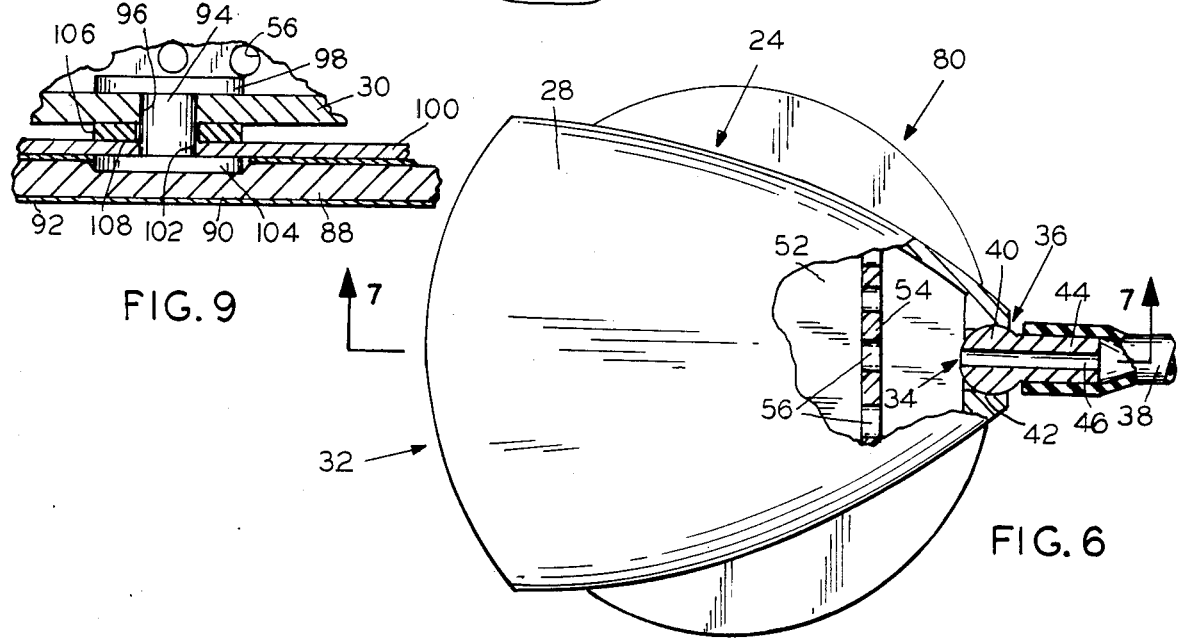
FIG. 9
FIG. 6
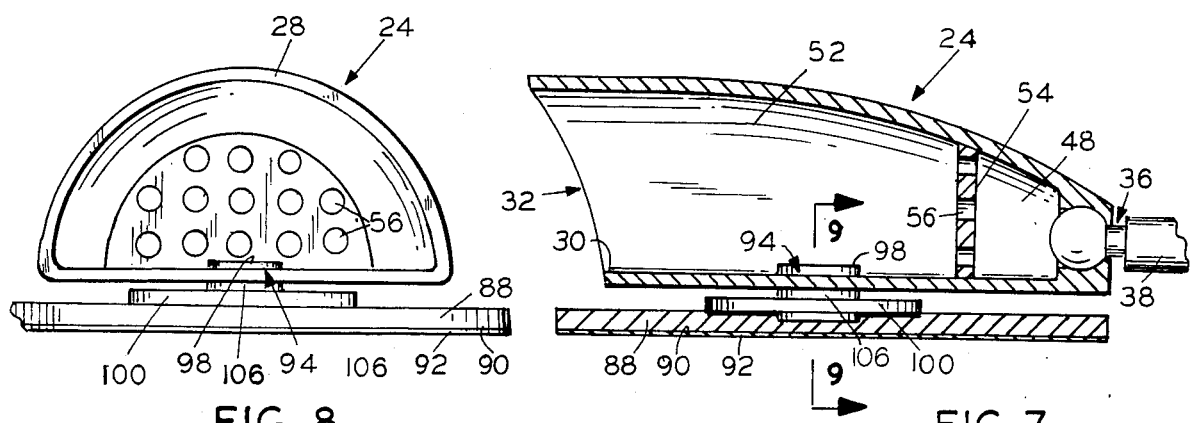
FIG. 8
FIG. 7

DEVICE FOR ADMINISTERING OXYGEN TO INFANTS DURING NURSING

BACKGROUND OF THE INVENTION

1. Field of the Invention

The present invention generally relates to oxygen adminstering devices, and more particularly, is concerned with a device which administers oxygen to infants while nursing.

2. Description of the Prior Art

Since the advent of positive pressure ventilation in the late 1960's, the mortality of those infants which require assisted ventilation has decreased drastically to the present day. However, this type of therapy is not without its hazards and complications, one of the major ones being damage to the tiny alveoli, reducing the number of functioning cells and requiring that the infants remain on oxygen therapy for long periods of time. In some cases, even years may be required to outgrow this need for supplemental oxygen. This need for oxygen necessitates that the infants be placed in incubators, or that oxygen hoods be placed around their heads, isolating them from the normal methods of infant feeding. An inability to hold and nurse the baby subverts an integral part of the parent-child bonding process.

It is well known that oxygen usage increases with the increased work of nursing, and that infants with low oxygen saturation cannot nurse adequately. Meeting this need for supplemental oxygen while being held and bottle or breast fed is awkward at best, with, for bottle feeding, three hands being needed to cradle baby, hold bottle and direct an oxygen tube at the infants nose with a certain degree of accuracy necessary to insure that the infant is indeed breathing oxygen enriched mixtures of air. Otherwise, the infant can decompensate rapidly, causing the feeding to be terminated and the infant unnecessary stress.

Oxygen cannulas, such as those used on adults, are unsatisfactory for infants, as all infants are obligate nose breathers up to three to six months of age. An oxygen cannula placed in the infant's nostrils will transmit distending pressure to the lungs. When a nipple is placed in the infant's mouth, this further complicates the matter by causing the infant to have greater difficulty exhaling. Large amounts of swallowed air creates over-distention of the stomach, causing discomfort and possible regurgitation. In addition, pressure that is transmitted to the lung can cause possible lung rupture.

A smooth, constant flow of oxygen, directed in front of the infant's nose, is the ideal and safest way to administer oxygen while the infant is nursing. It is the object of this invention to provide a device to make oxygen administration while nursing a simple and safe procedure.

SUMMARY OF THE INVENTION

The present invention provides a device for the administration of oxygen to nursing infants. A flow-directing member, having an inlet opening for connection with oxygen-supplying tubing and an internal plate with a plurality of holes formed therein to regulate the flow of oxygen, is attached onto the source of milk or other liquid so as to direct the oxygen onto the nostrils of the nursing infant.

The flow-directing member includes a curved surface which intersects with a flat surface to provide essentially a half-funnel configuration having a smaller inlet opening where the oxygen-supplying tubing is connected, and a larger, generally semicircular outlet opening.

In the embodiment preferred for bottle nursing, the curved surface of the flow-directing member extends beyond its intersection with the flat floor surface, so as to provide connection tabs for attachment to a flexible, contoured foam member which fits closely about a portion of the neck of the bottle. An adhesive strip which is attached to the foam member extends and adheres to the remainder of the neck of the bottle. The connection between the connection tabs of the flow-directing member and the bottle-neck-encircling contoured foam with adhesive strip may be pivoted to allow the flow-directing member to be rotated fowards or backwards to permit adjustment of the direction of oxygen flow.

In the preferred embodiment designed for breast feeding, a curved surface intersects with a flat surface so as to form a half-funnel shape for the flow directing member. In this embodiment, however, the flow-directing member is attached to a soft, flexible, breast conforming pad, having an adhesive backing for temporary attachment to the breast. A single fastener, centrally attached between the floor of the flow-directing member and the breast conforming pad, connects the flow-directing member to the breast. Such connection may use an attachment fastener which permits rotation in the plane of the floor of the flow-directing member, that is, from side to side, so as to permit adjustable direction of the oxygen towards the nostrils of the nursing infant.

BRIEF DESCRIPTION OF THE DRAWINGS

FIG. 1 illustrates a perspective view of the bottle feeding embodiment of the device for administering oxygen to infants while nursing.

FIG. 2 illustrates a front view of the bottle feeding embodiment of FIG. 1, without details of the feeding bottle.

FIG. 3 illustrates a cross-sectional view of the bottle feeding embodiment, as shown at line 3—3 of FIG. 2.

FIG. 4 illustrates a preferred manner of attachment of the flow-directing member of the bottle feeding embodiment, as shown as line 4—4 of FIG. 3.

FIG. 5 illustrates the breast feeding embodiment of the device for administering oxygen to infants while nursing, as the device would be used.

FIG. 6 illustrates a top view of the breast feeding embodiment of FIG. 5, with a section partially broken away.

FIG. 7 illustrates an elevation cross-section of the breast feeding embodiment as seen at line 7—7 of FIG. 6.

FIG. 8 illustrates a front view of the breast feeding embodiment, showing the outlet thereof.

FIG. 9 shows the preferred manner of attachment of the flow-directing member of the breast feeding embodiment, as seen at line 9—9 of FIG. 7.

DESCRIPTION OF THE PREFERRED EMBODIMENT

The device for administering oxygen to infants during nursing has two alternative configurations, depending on whether the infant is nursing from a bottle or from the breast.

Referring now to the drawings, and more particularly to FIG. 1, there is shown, in use, the preferred embodiment of the bottle nursing configuration 10. A standard feeding bottle 12 for infants is shown; however, with appropriate sizing, a smaller "premature infant" size of the nursing bottle configuration 10 that would attach to graduated feeders used to nurse prematures is within the scope of this invention. The bottle 12 has the normal neck 14, cap 16, and nipple 18. A nursing baby 20 is shown with the flow-directing member 24 directing oxygen directly to the vicinity of the infant's nostrils 26.

As seen in FIG. 1, FIG. 2 and FIG. 3, the flow-directing member 24 is comprised of a curved surface 28 intersecting with a flat floor surface 30 to provide a half-funnel shape having an outlet opening 32 of generally semicircular cross section and a smaller inlet opening 34 which, by means of a connecting member 36, is attached to a tube 38 leading to a supply of warmed oxygen (not shown).

The preferred embodiment of the connecting member 36 provides a ball swivel 40 which fits within a concave surrounding surface 42 at the inlet opening 34 of the flow-directing member 24. The ball swivel 40 and an attached neck 44 have an opening 46 formed therethrough for the passage of oxygen from the tubing 38 to the inlet chamber 48 of the flow directing member 24. The tubing 38 is tightly fit over the neck 44 of the connecting member 36, as such tubing is commonly attached to fixtures.

Within the flow-directing member 24, separating the inlet chamber 48 from the outlet chamber 52, is located a flow regulating plate 54 in which are formed a plurality of small holes 56 so as to regulate the flow of oxygen through the flow-directing member 24.

In the bottle nursing configuration 10, the curved surface 28 of the flow-directing member 24 extends beyond the intersection 58 with the floor surface 30 so as to provide connection tabs 60 for attachment. Attachment means to the neck 14 of the bottle 12 are provided, in the preferred embodiment, by a semicircularly contoured pad 64, preferably formed of a high density foam for flexibility and compressibility. An adhesive strip 66 is attached to the outer surface of the contoured pad 64 and extends beyond the ends 68 of that pad 64 so as to provide adhesive tabs 70 by which to fasten the contoured pad 64 securely about the neck 14 of the bottle 12. The adhesive tabs 70 are intended to be pulled tightly about the neck, thus compressing the foam pad 64 against the neck 14, the adhesive tabs 70 preferably overlapping each other in the process.

FIG. 4 illustrates the preferred manner of attachment of the connection tabs 60 of the flow-directing member 24 to the contoured pad 64 and adhesive strip 66. A rivet-type fastener 72 is passed through the pad 64, adhesive strip 66 and connection tabs 60. A washer 74 is located between the adhesive strip 66 and the connection tabs 60 so as to provide bearing surfaces 76 for the rotation or pivoting of the connection tabs 60, and thus rotation of the the flow-directing member 24 with relation to the nipple 18 and the location of the nostrils 26 of the infant 20.

The bottle nursing configuration 10 therefore is held firmly to the neck 14 of the bottle 12, but with the capability to be adjusted forwards or backwards to direct the oxygen as desired for the supplementation of the infant's air.

While FIG. 1 through FIG. 4 illustrate the bottle feeding configuration, FIG. 5 through FIG. 9 show the breast feeding configuration 80. The general form of the flow-directing member 24 is common to both configurations 10 and 80, the basic difference being the manner of attachment to the different nursing sources, the bottle 12 and the breast 84. Thus those portions common to both configurations, 10 and 80, retain the same reference numbers.

Referring to FIG. 5, there is shown, in use, the preferred embodiment of the breast nursing configuration 80. The mother 82 is shown holding the nursing infant 20 to her breast 84. The breast nursing configuration 80 is temporarily adhered to the nursing breast 84 so that the flow of oxygen from the outlet opening 32 of the flow directing member 24 is directed to the vicinity of the infants nostrils 26. An inlet opening 34 is connected to a tube 38, shown passing over the shoulder 86 of the mother 82 to a supply of warmed oxygen (not shown).

FIGS. 6, 7, and 8 provide greater detail regarding the breast feeding configuration 80. As in the bottle feeding configuration 10, a flow-directing member 24 is comprised of a curved surface 28 intersecting with a flat floor surface 30 to provide a half-funnel shape having an outlet opening 32 of generally semicircular cross section, and a smaller inlet opening 34 whereat a connecting member 36 is attached to a tube 38, as noted above. The connecting member 36 provides a ball swivel 40 which fits within a concave surrounding surface 42 at the inlet opening 34 of the flow-directing member 24. The ball swivel 40 and an attached neck 44 have an opening 46 formed therethrough for the passage of oxygen from the tubing 38 to the inlet chamber 48 of the flow directing member 24. The tubing 38 is tightly fit over the neck 44 of the connecting member 36.

Within the flow-directing member 24 of the breast feeding configuration 80, separating the inlet chamber 48 from the outlet chamber 52, is located a flow regulating plate 54 in which are formed a plurality of small holes 56 so as to regulate the flow of oxygen through the flow-directing member 24.

In the breast feeding configuration 80, the flow-directing member 24, as described above, is attached to the breast 84 by means of a soft, flexible, hypo-allergenic, breast conforming pad 88, having an adhesive surface 90 which, when not in use, is protected by a peel-off covering 92, as is common with adhesive surfaces. The adhesive pad 88, upon application, conforms to the contour of the breast 84 and allows placement appropriate to the direction of supplemental oxygen to the vicinity of the nursing infant's nostrils 26.

As best seen in FIG. 9, the preferred manner of attachment of the flow-directing member 80 to the adhesive pad 88 is by means of a single rivet-like fastener 94 which extends through a hole 96 formed centrally in the floor 30 of the flow-directing member 24. An upper lip 98 of the rivet-like fastener 94 holds the fastener 94 to the floor 30. A smaller, firmer pad 100, with a hole 102 centrally formed therein, is attached, by glue or otherwise, at the center of the adhesive pad 88, holding between pad 100 and pad 88 the lower lip 104 of the rivet-like fastener 94. A washer 106 is located between pad 100 and the floor 30 of the flow-directing member 24 to provide a bearing surface 108 to more readily permit rotation of the flow-directing member about the single fastener 94, from side to side in the plane of the floor 30, in a turret-like manner.

Thus, the breast nursing configuration 80 may be held firmly to the nursing breast, 84 at an appropriate position so as to direct supplemental oxygen to the vicinity of the infant's nostrils 26, but with the additional capability of turrel-like movement from side to side to adjust the direction of flow without repositioning the adhesive pad 88 on the mother's breast 84.

It is anticipated that the above described device for administering oxygen to nursing infants will be produced and marketed so as to be disposable, as is becoming more common, especially with devices used in hospitals, and thus would be made of materials, generally plastics, suitable for limited use and subsequent disposal. However, it is also possible that the above described devices may be produced and marketed for multiple-use application, particularly at home, where the flow-directing member 24 would be made of injection molded plastics suitable for home sterilization, as are the standard nursing bottles. In such instances, it is anticipated that the attachment means to the breast 84 or bottle 12, involving adhesives and foam pads, would be discarded, while the flow-directing portion would be reused, after appropriate sterilization. In such case, the rivet-like fasteners would be separable and easily assembled, as would be provided by the provision of threads attaching the separate parts of the fastener, so as to permit replacement of the disposable attachment means. The construction of such assemblable fasteners is not considered inventive, but it is clear that the use of such assemblable fasteners in either configuration is within the scope of the invention.

It is thought that the device for administering oxygen to nursing infants of the present invention and its many attendant advantages will be understood from the foregoing description and that it will be apparent that various changes may be made in form, construction and arrangement of the parts thereof without departing from the spirit and scope of the invention or sacrificing all of its material advantages, the forms hereinbefore stated being merely exemplary embodiments thereof.

We claim:

1. A device for administering oxygen to nursing infants, receiving milk or other liquid from a feeding bottle, having a neck, comprising:
   (a) tubing supplying oxygen from a source of oxygen;
   (b) a flow-directing member which includes:
      (1) a curved surface joining with a flat suface at its intersection therewith, so as to provide essentially a half-funnel configuration, wherein at one end there is a small inlet opening where the said oxygen-supplying tubing is connected, and at the other end a larger, generally semi-circular outlet opening; and
      (2) the said curved surface extending down beyond the said intersections with the said flat surface so as to provide connection tabs for attachment;
   (c) means for connecting said oxygen-supplying tubing to said inlet of said flow-directing member;
   (d) a plate having a plurality of holes formed therein, said plate being located within the said flow-directing member so as to regulate the flow of oxygen therethrough;
   (e) attachment means removably connected to said feeding bottle, comprising:
      (1) a flexible pad member, having an inner surface and an outer surface, the said inner surface contoured in semi-circular shape to fit closely about a portion of the said neck of said feeding bottle; and
      (2) adhesive strip means, attached to said flexible pad member and extending beyond the said flexible pad member so as to be adherably wrappable about an additional portion of the said neck of said bottle, thereby holding the said flexible pad member securely on the neck of said bottle; and,
   (f) two rotation permitting fasteners, located at separated positions on substantially opposing sides of the said neck of said feeding bottle, which rotatingly connect the said connection tabs of the said flow-directing member to the said attachment means removably connected to the said feeding bottle, so as to permit adjustment of the direction of oxygen flow onto the nostrils of the nursing infant by pivoting forwards or backwards the said flow directing member.

2. A device for administering oxygen to nursing infants, receiving milk from a human breast comprising:
   (a) tubing supplying oxygen from a source of oxygen;
   (b) a flow-directing member which includes:
      a curved surface joining with a flat floor surface so as to provide essentially a half-funnel configuration, wherein at one end there is a small inlet opening where the said oxygen-supplying tubing is connected, and at the other a larger, generally semi-circular outlet opening;
   (c) means for connecting said oxygen-supplying tubing to said inlet of said flow-directing member;
   (d) a plate having a plurality of holes formed therein, said late being located within the said flow-directing member so as to regulate the flow of oxygen therethrough;
   (e) attachment means removably connected to said human breast, comprising a breast conforming pad having adhesive backing for temporary attachment to said breast; and,
   (f) means for pivotally connecting the said flow-directing member to the said breast conforming pad, which means include a single rotation permitting fastener, having an axis, a first end, and a second end, the said first end of said fastener being attached to the said flat floor surface of the said flow-directing member and the said second end of said fastener being attached to the said breast conforming pad, so that the said flow-directing member rotates about the said axis of the said rotation pemitting fastener in a turret-like manner, thus allowing the said outlet opening of the said flow-directing member to be oriented to supply oxygen onto the nostrils of the nursing infant.

3. A device for administering oxygen to nursing infants, receiving milk or other liquid from a nursing source, comprising:
   (a) tubing supplying oxygen from a source of oxygen;
   (b) flow-directing member, having an opening for an outlet and an opening for an inlet;
   (c) means for connecting said oxygen-supplying tubing to said inlet of said flow-directing member;
   (d) a plate having a plurality of holes formed therein, said plate being located within the said flow-directing member so as to regulate the flow of oxygen therethrough; and
   (e) means for attaching said flow-directing member onto said nursing source, when the said nursing source is a feeding bottle, having a neck, which means include:

(1) connection tabs extending from the said flow-directing member;

(2) a flexible pad member, having an inner surface and an outer surface, the said inner surface contoured in semi-circular shape to fit closely about a portion of the said neck of said feeding bottle;

(3) adhesive strip means, attached to said flexible pad member and extending beyond the said flexible pad member so as to be adherably wrappable about an additional portion of the said neck of said bottle, thereby holding the said flexible pad member securely on the neck of said bottle; and (4) means for attaching the said connection tabs of the said flow-directing member onto the said outside surface of the said flexible pad member.

4. A device for administering oxygen to nursing infants, receiving milk or other liquid from a nursing source, comprising:

(a) tubing supplying oxygen from a source of oxygen;

(b) a flow-dircting member, having an opening for an outlet and an opening for an inlet;

(c) means for connecting said oxygen-supplying tubing to said inlet of said flow-directing member;

(d) a plate having a plurality of holes formed therein, said plate being located within the said flow-directing member so as to regulate the flow of oxygen therethrough;

(e) means for attaching said flow-directing member onto said nursing source; and (f) means for adjusting the orientation of said outlet of said flow-directing member, when the said nursing source is a feeding bottle, having a neck, which means include:

(1) connection tabs extending from the said flow-directing member;

(2) a neck member, fitting securely about the said neck of said feeding bottle; and (3) means for pivotally connecting the said connection tabs of the said flow-directing member to the said neck member, which means include two rotation permitting fasteners, which connect the said connection tabs to the said neck member, said rotation permitting fasteners being located at separated positions substantially on opposing sides of the said neck of said feeding bottle, so that the said flow-directing member may be pivoted, on said rotation premitting fasteners, forwards or backwards to adjust the direction of oxygen flow onto the nostrils of the nursing infant.

5. A device for administering oxygen to nursing infants, receiving milk or other liquid from a nursing source, comprising:

(a) tubing supplying oxygen from a source of oxygen;

(b) a flow-directing member, having an opening for an outlet and an opening for an inlet;

(c) means for connecting said oxygen-supplying tubing to said inlet to said flow-directing member;

(d) a plate having a plurality of holes formed therein, said plate being located within the said flow-directing member so as to regulate the flow of oxygen therethrough; and (e) means for attaching said flow-directing member onto said nursing source, when the said nursing source is a human breast, which means include:

(1) a breast conforming pad having adhesive backing for temporary attachment to said breast; and (2) means for attaching the said flow-directing member to the said breast conforming pad.

6. A device for administering oxygen to nursing infants, receiving milk or other liquid from a nursing source, comprising:

(a) tubing supplying oxygen from a source of oxygen;

(b) a flow-directing member, having an opening for an outlet and an opening for an inlet;

(c) means for connecting said oxygen-supplying tubing to said inlet to said flow-directing member;

(d) a plate having a plurality of holes formed therein, said plate being located within the said flow-directing member so as to regulate the flow of oxygen therethrough;

(e) means for attaching said flow-directing member onto said nursing source; and (f) means for adjusting the orientation of said outlet of said flow-directing member, when the said nursing source is the human breast, which means include:

(1) a breast conforming pad having adhesive backing for temporary attachment to the said breast; and (2) means of pivotally connecting the said flow-directing member to the said breast conforming pad, which connecting means includes a single rotation permitting fastener, having an axis, a first end, and a second end, the said first end of said fastener being attached to the said flow-directing member and the said second end being attached to the said breast conforming pad so that the said flow-directing member rotates about the said axis of the said fastener from side to side in a turret-like manner, thus allowing the said flow-directing member to be oriented to supply oxygen onto the nostrils of the nursing infant.

7. A device for administering oxygen to nursing infants, receiving milk or other liquid from a nursing source, comprising:

(a) tubing supplying oxygen from a source of oxygen;

(b) a flow-directing member, having an opening for an outlet and an opening for an inlet;

(c) means for connecting said oxygen-supplying tubing to said inlet of said flow-directing member; and (d) means for attaching said flow-directing member onto said nursing source, when the said nursing source is a feeding bottle, having a neck, which means includes:

(1) connection tabs extending from the said flow-directing member;

(2) a flexible pad member, having an inner surface and an outer surface, the said inner surface contoured in semi-circular shape to fit closely about a portion of the said neck of said feeding bottle;

(3) adhesive strip means, attached to said flexible pad member and extending beyond the said flexible pad member so as to be adherably wrappable about an additional portion of the said neck of said bottle, thereby holding the said flexible pad member securely on the neck of said bottle; and (4) means of attaching the said connection tabs of the said flow-directing member onto the said outside surface of the said flexible pad member.

8. A device for administering oxygen to nursing infants, receiving milk or other liquid from a nursing source, comprising:

(a) tubing supplying oxygen from a source of oxygen;

(b) a flow-directing member, having an opening for an outlet and an opening for an inlet;

(c) means for connecting said oxygen-supplying tubing to said inlet of said flow-directing member;

(d) means for attaching said flow-directing member onto said nursing source; and (e) means for adjusting the orientation of said outlet of said flow-directing member, when the said nursing source is a feeding bottle, having a neck, which means include:

(1) connection tabs extending from the said flow-directing member;

(2) a neck member, fitting securely about the said neck of said feeding bottle; and (3) means of pivotally connecting the said connection tabs of the said flow-directing member to the said neck member, which means include two rotation permitting fasteners, which connect the said connection tabs to the said neck member, said rotation permitting fasteners being located at separated positions substantially on opposing sides of the said neck of said feeding bottle, so that the said flow-directing member may be pivoted, on said rotation permitting fasteners, forwards or backwards to adjust the direction of oxygen flow onto the nostrils of the nursing infant.

9. A device for administering oxygen to nursing infants, receiving milk or other liquid from a nursing source, comprising:

(a) tubing supplying oxygen from a source of oxygen;

(b) a flow-directing member, having an opening for an outlet and an opening for an inlet;

(c) means for connecting said oxygen-supplying tubing to said inlet of said flow-directing member; and (d) means for attaching said flow-directing member onto said nursing source, when the said nursing source is a human breast, which means include:

(1) a breast conforming pad having adhesive backing for temporary attachment to said breast; and (2) means of attaching the said flow-directing member to the said breast conforming pad.

10. A device for administering oxygen to nursing infants, receiving milk or other liquid from a nursing source, comprising:

(a) tubing supplying oxygen from a source of oxygen;

(b) a flow-directing member, having an opening for an outlet and an opening for an inlet;

(c) means for connecting said oxygen-supplying tubing to said inlet to said flow-directing member;

(d) means for attaching said flow-directing member onto said nursing source; and (e) means for adjusting the orientation of said outlet of said flow-directing member, when the said nursing source is the human breast, which means include:

(1) a breast conforming pad having adhesive backing for temporary attachment to the said breast; and (2) means of pivotally connecting the said flow-directing member to the said breast conforming pad, which connecting means include a single rotation permitting fastener, having an axis, a first end, and a second end, the said first end of said fastener being attached to the said flow-directing member and the said second end being attached to the said breast conforming pad so that the said flow-directing member rotates about the said axis of the said fastener from side to side in a turret-like manner, thus allowing the said flow-directing member to be oriented to supply oxygen onto the nostrils of the nursing infant.

* * * * *